(12) United States Patent
Daniel et al.

(10) Patent No.: US 7,183,360 B2
(45) Date of Patent: Feb. 27, 2007

(54) METHOD FOR CROSSLINKING HYDROGELS WITH MORPHOLINE-2,3-DIONES

(75) Inventors: Thomas Daniel, Waldsee (DE); Kai Michael Exner, Eppelheim (DE); Klemens Massonne, Bad Dürkheim (DE); Ulrich Riegel, Frankfurt (DE); Matthias Weismantel, Jossgrund (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 305 days.

(21) Appl. No.: 10/491,204

(22) PCT Filed: Sep. 27, 2002

(86) PCT No.: PCT/EP02/10866

§ 371 (c)(1),
(2), (4) Date: Mar. 26, 2004

(87) PCT Pub. No.: WO03/031482

PCT Pub. Date: Apr. 17, 2003

(65) Prior Publication Data

US 2004/0231065 A1 Nov. 25, 2004

(30) Foreign Application Priority Data

Oct. 5, 2001 (DE) ................ 101 49 267

(51) Int. Cl.
C08F 8/32 (2006.01)

(52) U.S. Cl. ............... 525/327.6; 525/329.9; 525/375; 525/374; 525/107

(58) Field of Classification Search ............. 525/327.6, 525/329.9, 375, 374, 107
See application file for complete search history.

(56) References Cited

U.S. PATENT DOCUMENTS 2,723,247 A * 11/1955 Harrington, Jr. ............. 524/96
4,666,983 A    5/1987 Tsubakimoto et al.
5,019,606 A    5/1991 Marten et al.
5,331,059 A    7/1994 Engelhardt et al.
5,385,983 A    1/1995 Graham
5,663,262 A *  9/1997 Shirakawa et al. ......... 526/312
6,239,230 B1   5/2001 Eckert et al.
6,472,478 B1 * 10/2002 Funk et al. ............... 525/327.6
6,503,979 B1 *  1/2003 Funk et al. ................ 524/556

FOREIGN PATENT DOCUMENTS

| EP | A 083 022 | 7/1983 |
| EP | A 349 935 | 1/1990 |
| EP | A 372 981 | 6/1990 |
| EP | A 530 438 | 3/1993 |
| EP | A 543 303 | 5/1993 |
| WO | WO 99 42494 A | 8/1999 |
| WO | WO 99 43720 A | 9/1999 |
| WO | WO 00 31152 | 6/2000 |
| WO | WO 00/31152 * | 6/2000 |
| WO | WO 00/31153 * | 6/2000 |
| WO | WO 00 31153 A | 6/2000 |
| WO | WO 00 34453 | 6/2000 |

OTHER PUBLICATIONS

Hardwood et al., "A Novel Synthetic Route to Morpholin-2,3-Diones from 2-Aminoalcohols", *Tetrahedron Letters*, Elsevier Science Publishers, Amsterdam, The Netherlands, Bd. 37, Nr. 24, pp. 4217-4220 (Jun. 10, 1996).

* cited by examiner

*Primary Examiner*—Ling-Sui Choi
(74) *Attorney, Agent, or Firm*—Marshall, Gerstein & Borun LLP

(57) ABSTRACT

The invention relates to a method for gel post-crosslinking or surface post-crosslinking water-absorbing hydogels with morpholine-2,3-diones, to the post-crosslinked hydrogels and to the use thereof.

13 Claims, No Drawings

METHOD FOR CROSSLINKING HYDROGELS WITH MORPHOLINE-2,3-DIONES

CROSS-REFERENCE TO RELATED APPLICATION

This is the U.S. national phase application of International Application No. PCT/EP02/10866, filed Sep. 27, 2002.

The present invention relates to a process for gel or surface postcrosslinking of water-absorbent hydrogels using morpholine-2,3-diones and to the postcrosslinked hydrogels and their use.

Swellable hydrogel-forming addition polymers, known as superabsorbent polymers or SAPs, are known from the prior art. They are networks of flexible hydrophilic addition polymers, which can be both ionic and nonionic in nature. They are capable of absorbing and binding aqueous fluids by forming a hydrogel and therefore are preferentially used for manufacturing tampons, diapers, sanitary napkins, incontinence articles, training pants for children, insoles and other hygiene articles for the absorption of body fluids. Superabsorbents are also used in other fields of technology where fluids, especially water or aqueous solutions, are absorbed. These fields include for example storage, packaging, transportation (packaging material for water-sensitive articles, for example flower transportation, shock protection); food sector (transportation of fish, fresh meat; absorption of water, blood in fresh fish/meat packs); medicine (wound plasters, water-absorbent material for burn dressings or for other weeping wounds); cosmetics (carrier material for pharmaceuticals and medicaments, rheumatic plasters, ultrasound gel, cooling gel, cosmetic thickeners, sunscreen); thickeners for oil/water or water/oil emulsions; textiles (gloves, sportswear, moisture regulation in textiles, shoe inserts); chemical process industry applications (catalyst for organic reactions, immobilization of large functional molecules (enzymes), adhesive for agglomerations, heat storage media, filtration aids, hydrophilic component in polymer laminates, dispersants, liquefiers); building construction, installation (powder injection molding, clay-based renders, vibration-inhibiting medium, assistants in relation to tunneling in water-rich ground, cable sheathing); water treatment, waste treatment, water removal (de-icers, reusable sandbags); cleaning; agriculture industry (irrigation, retention of meltwater and dew precipitates, composting additive, protection of forests against fungal and insect infestation, delayed release of active ingredients to plants); fire protection (flying sparks)(covering houses or house walls with SAP gel, since water has a very high heat capacity, ignition can be prevented; spraying of SAP gel in the case of fires such as for example forest fires); coextrusion agent in thermoplastic polymers (hydrophilicization of multilayer) films; production of films and thermoplastic moldings capable of absorbing water (for example agricultural films capable of storing rain and dew water; SAP-containing films for keeping fresh fruit and vegetables which can be packed in moist films; the SAP stores water released by the fruit and vegetables without forming condensation droplets and partly reemits the water to the fruit and vegetables, so that neither fouling nor wilting occurs; SAP-polystyrene coextrudates for example for food packs such as meat, fish, poultry, fruit and vegetables); carrier substance in active-ingredient formulations (drugs, crop protection). Within hygiene articles, superabsorbents are generally positioned in an absorbent core which, as well as SAP, comprises other materials, including fibers (cellulose fibers), which act as a kind of liquid buffer to intermediately store the spontaneously applied liquid insults and are intended to ensure efficient channelization of the body fluids in the absorbent core toward the superabsorbent.

The current trend in diaper design is toward ever thinner constructions having a reduced cellulose fiber content and an increased hydrogel content. The trend toward ever thinner diaper constructions has substantially changed the performance profile required of the water swellable hydrophilic polymers over the years. Whereas at the start of the development of highly absorbent hydrogels it was initially solely the very high swellability on which interest focused, it was subsequently determined that the ability of the superabsorbent to transmit and distribute fluid is also of decisive importance. It has been determined that conventional superabsorbents greatly swell at the surface on wetting with liquid, so that transportation of liquid into the particle interior is substantially compromised or completely prevented. This trait of superabsorbents is known as gel blocking. The greater amount of polymer per unit area in the hygiene article must not cause the swollen polymer to form a barrier layer to subsequent fluid. A product having good transportation properties will ensure optimal utilization of the entire hygiene article. This prevents the phenomenon of gel blocking, which in the extreme case will cause the hygiene article to leak. Fluid transmission and distribution is thus of decisive importance with regard to the initial absorption of body fluids.

Good transportation properties are possessed for example by hydrogels having high gel strength in the swollen state. Gels lacking in strength are deformable under an applied pressure (pressure due to bodyweight) and clog the pores in the SAP/cellulose fiber absorbent and so prevent continued absorption of fluid. Enhanced gel strength is generally obtained through a higher degree of crosslinking, although this reduces retention performance. An elegant way to enhance gel strength is surface postcrosslinking. In this process, dried superabsorbents having an average crosslink density are subjected to an additional crosslinking step. Surface postcrosslinking increases the crosslink density in the sheath of the superabsorbent particle, whereby the absorbency under load is raised to a higher level. Whereas the absorption capacity decreases in the superabsorbent particle sheath, the core has an improved absorption capacity (compared to the sheath) owing to the presence of mobile polymer chains, so that sheath construction ensures improved fluid transmission without occurrence of the gel blocking effect. It is perfectly desirable for the total capacity of the superabsorbent to be occupied not spontaneously but with time delay. Since the hygiene article is generally repeatedly insulted with urine, the absorption capacity of the superabsorbent should sensibly not be exhausted after the first disposition.

Hydrophilic, superabsorbent hydrogels are in particular polymers of (co)polymerized hydrophilic monomers, graft copolymers of one or more hydrophilic monomers on a suitable grafting base, crosslinked cellulose or starch ethers, crosslinked carboxymethylcellulose, partially crosslinked polyalkylene oxide or natural products that are swellable in aqueous liquids, for example guar derivatives. Hydrogels of this kind are used as products for absorbing aqueous solutions in the production of diapers, tampons, sanitary napkins and other hygiene articles, and as water retainers in market gardening.

To improve service properties such as diaper rewet and AUL, for example, hydrophilic, superabsorbent hydrogels are generally subjected to surface or gel postcrosslinking.

This postcrosslinking is known to one skilled in the art and is preferably carried out in aqueous gel phase or as surface postcrosslinking of the ground and screened polymer particles.

Useful crosslinkers for this purpose include compounds containing at least two groups capable of forming covalent bonds with the carboxyl groups of the hydrophilic polymer. Useful compounds include for example di- and polyglycidyl compounds, such as diglycidyl phosphonate, alkoxysilyl compounds, polyaziridines, polyamines or polyamidoamines, and these compounds can also be used in mixtures with one another (see for example EP-A-0 083 022, EP-A-0 543303 and EP-A-0 530 438). Polyamidoamine crosslinkers are described in EP-A-0 349 935 in particular.

A major disadvantage of these crosslinkers is their high reactivity since it necessitates special safety precautions in commercial operation in order that undesirable side effects may be avoided. Similarly, the aforementioned crosslinkers have skin-irritating properties, which makes their use in hygiene articles appear to be problematical.

Known crosslinkers further include polyfunctional alcohols. For instance, EP-A-0 372 981, U.S. Pat. No. 4,666,983 and U.S. Pat. No. 5,385,983 teach the use of hydrophilic polyalcohols and the use of polyhydroxy surfactants respectively. The reaction in these references is carried out at high temperatures of 120–250° C. The process has the disadvantage that the crosslinking esterification itself proceeds only slowly at these temperatures.

Further crosslinkers which have been described as suitable include 2-oxazolidone and its derivatives in WO 99/42494, 2-oxotetrahydro-1,3-oxazine and its derivatives in WO 00/31153, N-acyl-2-oxazolidones in WO 00/31152 and bis- and poly-2-oxazolidinones in WO 99/43720. True, they meet the requirements regarding use in hygiene articles, but are not commercially available as compounds and are fairly difficult to prepare pure.

Crosslinkers which have been described further include β-hydroxyalkylamides in U.S. Pat. No. 6,239,230. These too are suitable for use in hygiene articles. The disadvantage of these compounds is the relatively high use levels required and the associated cost.

It is an object of the present invention to provide further crosslinking substances for superabsorbents that may be used in a very short reaction time and at very low reaction temperatures.

We have found that this object is achieved, surprisingly, when morpholine-2,3-diones are used as crosslinkers.

Morpholine-2,3-diones are known per se from the literature as starting materials for preparing certain oxamic acid derivatives EP 371640.

The present invention accordingly provides processes for crosslinking starting polymers for preparing hydrogel-forming polymers capable of absorbing aqueous fluids, which comprises using a crosslinker of the general formula 1:

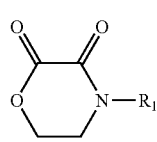

(Formula 1)

where $R_1$ is hydrogen, $C_1$–$C_4$-alkyl, $C_1$–$C_4$-hydroxyalkyl or a group of the formula 2:

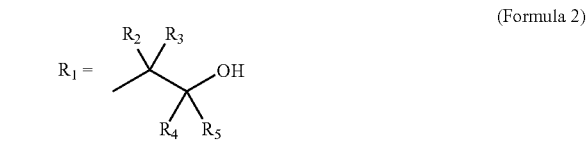

(Formula 2)

where $R_2$, $R_3$, $R_4$, and $R_5$ are each independently $C_1$–$C_4$-alkyl, $C_1$–$C_4$-hydroxyalkyl or hydrogen. Crosslinking comprehends not only gel crosslinking (crosslinking of linear or lightly crosslinked polymer) but also surface postcrosslinking. Surface postcrosslinking is the surficially stronger crosslinking of the starting polymer that leads to a core-sheath structure. By starting polymer is meant the polymer prior to crosslinking. Hydrogel-forming polymers capable of absorbing aqueous fluids are preferably those which absorb at least their own weight and preferably 10 times their own weight of distilled water, preferably even under a pressure of 0.7 psi.

Surface postcrosslinking is preferred. The starting polymer preferably contains carboxyl groups.

In the above-described crosslinking processes, the starting polymer is treated with a crosslinker and preferably post-crosslinked and dried by raising the temperature during or after the treatment, the crosslinker preferably being present in an inert solvent. Inert solvents are solvents which substantially do not react either with the starting polymer or with the crosslinker. Preference is given to such solvents which do not react chemically with the starting polymer or with the crosslinker to an extent of more than 90%, preferably more than 95%, particularly preferably more than 99%, especially to an extent of more than 99.5%.

A particularly preferred crosslinker in the above processes is N-2-hydroxyethylmorpholine-2,3-dione (formula 3):

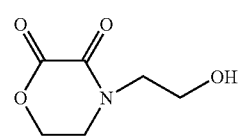

(Formula 3)

It is particularly simple and inexpensive to prepare.

Postcrosslinking and drying is preferably carried out at from 30 to 250° C., especially at from 50–200° C. and most preferably at from 100–180° C. The surface postcrosslinking solution is preferably applied by spraying the polymer in suitable spray mixers. After spraying, the polymer powder is thermally dried, and the crosslinking reaction can take place not only before but also during the drying operation. Preference is given to spraying a solution of the crosslinker in reaction mixers or mixing and drying ranges such as for example Lödige mixers, BEPEX mixers, NAUTA mixers, SHUGGI mixers or PROCESSALL. It is moreover also possible to use fluidized bed dryers.

The drying operation can take place in the mixer itself, by heating of the jacket or by blowing in hot air. Also suitable is a downstream dryer such as for example a shelf dryer, a rotary tube oven or a heatable screw. But is is also possible to utilize an azeotropic distillation as drying technique, for example. The residence time at this temperature in the reaction mixer or dryer is preferably below 60 min and more preferably below 30 min.

Preference is given to the above processes wherein the starting polymer is a polymeric acrylic acid or a polyacrylate, especially a polymeric acrylic acid or a polyacrylate obtained by free-radical polymerization using a polyfunctional ethylenically unsaturated free-radical crosslinker.

The present invention also provides a composition of matter comprising a crosslinker of the formula 1 or the preferred crosslinker and solvents selected from the group consisting of water, a mixture of water with one or more organic solvents having unlimited solubility in water, and a mixture of water with one or more monohydric or polyhydric alcohols, for example methanol and glycerol. The alcohols preferably bear 1, 2 or 3 OH groups and preferably have from 1 to 10 and especially up to 4 carbon atoms. Preference is given to primary and secondary alcohols.

In the composition of matter, the solvent is preferably an alcohol-water mixture having an alcohol content of 10–90% by weight, preferably 30–70% by weight, more preferably 15–65% by weight and especially 40–60% by weight, based on this solution.

Preferred alcohols are methanol, ethanol, isopropanol, ethylene glycol, 1,2-propanediol or 1,3-propanediol.

The preferred composition of matter includes from 0.1 to 20% by weight, especially from 0.5 to 10 and especially up to 3% by weight of crosslinker.

The above processes preferably utilize an abovementioned composition of matter.

Preference is given to those processes utilizing the composition of matter comprising crosslinker and solvent in a ratio of 0.1–20% by weight and especially 0.5–10% by weight, based on the mass of the starting polymer.

Preference is given to those processes utilizing the crosslinker in a dose of 0.01–5.0% by weight, preferably 0.02–3.0% by weight, more preferably 0.03–1.0% by weight and especially 0.05–0.1% by weight, based on the starting polymer.

The present invention also provides polymers produced by one of the abovementioned processes and their use in hygiene articles, packaging materials and nonwovens and also the use of an abovementioned composition of matter for producing crosslinked polymers or polymers capable of being crosslinked by heating, especially in coatings and paints.

The hydrophilic superabsorbent hydrogels (starting polymers) to be used in the process of the invention are in particular polymers of (co)polymerized hydrophilic monomers, graft (co)polymers of one or more hydrophilic monomers on a suitable grafting base, crosslinked cellulose or starch ethers or natural products that are swellable in aqueous fluids, for example guar derivatives. These hydrogels are known to one skilled in the art and are described for example in U.S. Pat. No. 4,286,082, DE-C-27 06 135, U.S. Pat. No. 4,340,706, DE-C-37 13 601, DE-C-28 40 010, DE-A-43 44 548, DE-A-40 20 780, DE-A-40 15 085, DE-A-39 17 846, DE-A-38 07 289, DE-A-35 33 337, DE-A-35 03 458, DE-A-42 44 548, DE-A-42 19 607, DE-A-40 21 847, DE-A-38 31 261, DE-A-35 11 086, DE-A-31 18 172, DE-A-30 28 043, DE-A-44 18 881, EP-A-0 801 483, EP-A-0 455 985, EP-A-0 467 073, EP-A-0 312 952, EP-A-0 205 874, EP-A-0 499 774, DE-A 26 12 846, DE-A-40 20 780, EP-A-0 20 5674, U.S. Pat. No. 5,145,906, EP-A-0 530 438, EP-A-0 670 073, U.S. Pat. No. 4,057,521, U.S. Pat. No. 4,062,817, U.S. Pat. No. 4,525,527, U.S. Pat. No. 4,295,987, U.S. Pat. No. 5,011,892, U.S. Pat. No. 4,076,663 or U.S. Pat. No. 4,931,497. Also of particular suitability are superabsorbent hydrogels from a manufacturing process as described in WO 01/38402 and also inorganic-organic hybridic superabsorbent hydrogels as described in DE 198 54 575. The content of the aforementioned patent documents, especially the hydrogels produced by the processes, are expressly incorporated herein by reference.

Examples of hydrophilic monomers suitable for preparing these hydrophilic superabsorbent hydrogels are polymerization-capable acids, such as acrylic acid, methacrylic acid, vinylsulfonic acid, vinylphosphonic acid, maleic acid including its anhydride, fumaric acid, itaconic acid, 2-acrylamido-2-methylpropanesulfonic acid, 2-acrylamido-2-methylpropanephosphonic acid and also their amides, hydroxyalkyl esters and amino- or ammonio-containing esters and amides. Also, water-soluble N-vinylamides or else diallyldimethylammonium chloride. Preferred hydrophilic monomers are compounds of the formula 4

(Formula 4)

where $R_1$ is hydrogen, methyl or ethyl, $R_2$ is —$COOR_4$, a sulfonyl group or a phosphonyl group, a ($C_1$–$C_4$)-alkanol-esterified phosphonyl group or a group of the formula 5

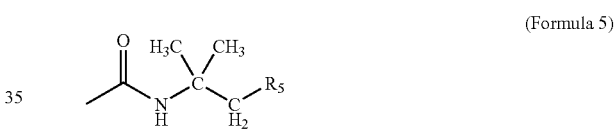

(Formula 5)

$R_3$ is hydrogen, methyl, ethyl or a carboxyl group, $R_4$ is hydrogen, amino, or hydroxy-($C_1$–$C_4$)-alkyl, and $R_5$ is a sulfonyl group, a phosphonyl group or a carboxyl group.

Examples of ($C_1$–$C_4$)-alkanols are methanol, ethanol, n-propanol or n-butanol.

Particularly preferred hydrophilic monomers are acrylic acid and methacrylic acid.

Suitable grafting bases for hydrophilic hydrogels obtainable by graft copolymerization of olefinically unsaturated acids may be natural or synthetic in origin. Examples are starch, cellulose or cellulose derivatives and also other polysaccharides and oligosaccharides, polyalkylene oxides, especially polyethylene oxides and polypropylene oxides, and also hydrophilic polyesters.

The water-absorbent polymer is obtainable via free-radical graft copolymerization of acrylic acid or acrylate onto a water-soluble polymer matrix. Suitable water-soluble polymer matrices include for example, but not exclusively, alginates, polyvinyl alcohol and polysaccharides such as for example starch. Graft copolymerization for the purposes of the present invention utilizes a polyfunctional ethylenically unsaturated free-radical crosslinker.

The water-absorbent polymer can be an organic-inorganic hybrid polymer formed from a polymeric acrylic acid or a polyacrylate on the one hand and a silicate, aluminate or aluminosilicate on the other. More particularly, it is possible to use polymeric acrylic acid or polyacrylate which were obtained via free-radical polymerization and in which a polyfunctional ethylenically unsaturated free-radical crosslinker was used and whose production process employed a water-soluble silicate or soluble aluminate or mixtures thereof.

Suitable polyalkylene oxides have for example the formula 6

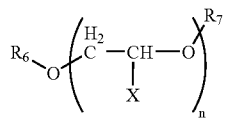

(Formula 6)

where $R_6$ and $R_7$ are each independently hydrogen, alkyl, alkenyl or aryl,

X is hydrogen or methyl, and n is an integer from 1 to 10 000.

$R_6$ and $R_7$ are each preferably hydrogen, $(C_1–C_4)$-alkyl, $(C_2–C_6)$-alkenyl or phenyl.

Preferred hydrogels are in particular polyacrylates, polymethyacrylates and also the graft polymers described in U.S. Pat. No. 4,931,497, U.S. Pat. No. 5,011,892 and U.S. Pat. No. 5,041,496. Very particularly preferred hydrogels are the kneader polymers described in WO 01/38402 and the hybrid organic-inorganic hydrogels based on polyacrylates that are described in DE 198 545 75.

The hydrophilic superabsorbent hydrogels are preferably in crosslinked form, ie they contain compounds having at least two double bonds which have been copolymerized into the polymer network. Suitable crosslinkers are in particular methylenebisacrylamide and methylenebismethacrylamide, esters of unsaturated mono- or polycarboxylic acids with polyols, such as diacrylate or triacrylate, examples being the diacrylates and dimethacrylates of butanediol with ethylene glycol and also trimethylolpropane triacrylate and allyl compounds such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A-0 343 427. However, the process of the invention particularly preferably utilizes the hydrogels prepared using polyallyl ethers as crosslinkers and by acidic homopolymerization of acrylic acid. Suitable crosslinkers are pentaerythritol triallyl ether, pentaerythritol tetraallyl ether, polyethylene glycol diallyl ether, monoethylene glycol diallyl ether, glycerol diallyl ether, glycerol triallyl ether, polyallyl ethers based on sorbitol and also ethoxylated variants thereof. Particular preference is further given to crosslinkers which are polyethylene glycol diacrylates, ethoxylated derivatives of trimethylolpropane triacrylate for example Sartomer SR 9035, and also ethoxylated derivatives of glycerol diacrylate and glycerol triacrylate. It will be appreciated that mixtures of the above crosslinkers can be used as well.

The water-absorbent polymer is preferably a polymeric acrylic acid or a polyacrylate. This water-absorbent polymer can be prepared by the method known from the literature. Preference is given to polymers containing crosslinking comonomers (0.001–10 mol %), but most preference is given to polymers which were obtained via free-radical polymerization and in which a polyfunctional ethylenically unsaturated free-radical crosslinker was used.

The hydrophilic superabsorbent hydrogels can be prepared by conventional polymerization processes. Preference is given to addition polymerization in aqueous solution by the process of gel polymerization. In this process, from 15 to 50% by weight aqueous solutions of one or more hydrophilic monomers and optionally of a suitable grafting base are polymerized in the presence of a free-radical initiator, preferably without mechanical mixing, utilizing the Trommsdorff-Norrish effect (Makromol. Chem. 1, 169 (1947)). The polymerization reaction can be conducted in the temperature range from 0° C. to 150° C., and preferably from 10° C. to 100° C., not only at atmospheric pressure but also under elevated or reduced pressure. As usual, the addition polymerization can also be carried out in a protective gas atmosphere, preferably under nitrogen. The addition polymerization can be initiated using high-energy electromagnetic radiation or the customary chemical polymerization initiators, for example organic peroxides, such as benzoyl peroxide, tert-butyl hydroperoxide, methyl ethyl ketone peroxide, cumene hydroperoxide, azo compounds such as azodiisobutyronitrile and also inorganic peroxo compounds such as $(NH_4)_2S_2O_8$. $K_2S_2O_8$ or $H_2O_2$.

They can if desired be used in combination with reducing agents such as for example ascorbic acid, sodium hydrogensulfite, and iron(ll) sulfate, or redox systems where the reducing component is an aliphatic or aromatic sulfinic acid, such as benzenesulfinic acid and toluenesulfinic acid or derivatives thereof, for example Mannich adducts of sulfinic acids, aldehydes and amino compounds as described in DE-C-1 301 566. The quality traits of the addition polymers can be further improved by supplementarily heating the polymer gels for a number of hours in the temperature range from 50° C. to 130° C. and preferably from 70° C. to 100° C.

The resultant gels are neutralized to the extent of 0–100 mol %, preferably 25–100 mol % and particularly preferably from 50–85 mol %, based on monomer used, for which the customary neutralizing agents can be employed, preferably alkali metal hydroxides, alkali metal oxides or the corresponding alkali metal carbonates, particularly preferably sodium hydroxide, sodium carbonate and sodium bicarbonate.

Neutralization is customarily achieved by mixing the neutralizing agent in as an aqueous solution or preferably as a solid. To this end, the gel is mechanically comminuted, by means of a meat grinder for example, and the neutralizing agent sprayed, scattered or poured on and then carefully mixed in. The neutralized gel material can then be repeatedly minced for homogenization. The neutralized gel material is then dried with a belt or can dryer until the residual moisture content is preferably below 10% by weight and especially below 5% by weight.

However, the addition polymerization can also be carried out by any other method described in the literature. More particularly, the neutralization of the acrylic acid can also be effected prior to the addition polymerization. The polymerization can then be carried out continuously or else batchwise in a belt reactor known to one skilled in the art or in a kneading reactor. When the polymerization is carried out in a belt reactor, it is particularly preferably initiated by means of electromagnetic radiation, preferably by means of UV radiation, or alternatively using a redox initiator system. Very particular preference is also given to the combination of the two initiation methods: electromagnetic radiation and chemical redox initiator system simultaneously.

The dried hydrogel is then ground and sieved, and the grinding may be customarily performed using roll mills, pin mills or vibrating mills. The preferred particle size for the sieved hydrogel is preferably in the range from 45–1000 µm, more preferably from 45–850 µm, particularly preferably from 200–850 µm, and most preferably from 300–850 µm. These ranges preferably cover 80% by weight of the particles and especially 90% by weight of the particles. The particle size distribution can be determined using established laser methods.

The CRC value [g/g] of the hydrogel-forming polymers according to the invention can be measured by the methods indicated in the description part and is preferably above 15, especially 16, 18, 20, 22, 24, or higher, particularly preferably 25 especially 26, 27, 28, 29, especially preferably 30, 31, 32, 33, 34, 35, 36, 37 or higher.

The AUL-0.7 psi value [g/g] of the hydrogel-forming polymers according to the invention can be measured by the methods indicated in the description part and is preferably above 8, especially 9, 10, 11, 12, 13, 14 or higher, more preferably 15 especially 16, 17, 18, 19, or higher, especially preferably greater than 20, especially 21, 22, 23, 24, 25, 26, 27, 28, or higher.

The AUL-0.5 psi value [g/g] of the hydrogel-forming polymers according to the invention can be measured by the methods indicated in the description part and is preferably above 8, especially 9, 10, 11, 12, 13, 14 or higher, more preferably 15 especially 16, 17, 18, 19, or higher, especially preferably greater than 20, especially 21, 22, 23, 24, 25, 26, 27, 28, or higher.

Deployment and use of subject hydrogel-forming polymer

The present invention further provides for the use of the abovementioned hydrogel-forming polymers in hygiene articles comprising
(A) a liquid pervious topsheet
(B) a liquid impervious backsheet
(C) a core positioned between (A) and (B) and comprising
  10–100% by weight of the hydrogel-forming polymer according to the invention
  0–90% by weight of hydrophilic fiber material preferably 20–100% by weight of the hydrogel-forming polymer according to the invention, 0–80% by weight of the hydrophilic fiber material
    more preferably 30–100% by weight of the hydrogel-forming polymer according to the invention, 0–70% by weight of the hydrophilic fiber material
    even more preferably 40–100% by weight of the hydrogel-forming polymer according to the invention, 0–60% by weight of the hydrophilic fiber material
    much more preferably 50–100% by weight of the hydrogel-forming polymer according to the invention,
    0–50% by weight of the hydrophilic fiber material particularly preferably 60–100% by weight of the hydrogel-forming polymer according to the invention,
    0–40% by weight of the hydrophilic fiber material especially preferably 70–100% by weight of the hydrogel-forming polymer according to the invention,
    0–30% by weight of the hydrophilic fiber material extremely preferably 80–100% by weight of the hydrogel-forming polymer according to the invention,
    0–20% by weight of the hydrophilic fiber material most preferably 90–100% by weight of the hydrogel-forming polymer according to the invention, 0–10% by weight of the hydrophilic fiber material
(D) optionally a tissue layer positioned directly above and below said core (C) and
(E) optionally an acquisition layer positioned between (A) and (C).

The percentages are to be understood so that in the case of 10–100% by weight 11, 12, 13, 14, 15, 16, 17, 18, 19 up to in each case 100% by weight of hydrogel-forming polymer according to the invention and all in between %ages (for example 12.2%) are possible and correspondingly hydrophilic fiber material from 0 to respectively 89, 88, 87, 86, 85, 83, 82, 81% by weight and in between percentages (for example 87.8%) are possible. If further materials are present in the core, the percentages of polymer and fiber decrease accordingly. The same applies to the preferred ranges, for example in the case of extremely preferably 81, 82, 83, 84, 85, 86, 87, 88, 89% by weight can be present for the hydrogel-forming polymer according to the invention and correspondingly 19, 18, 17, 16, 15, 14, 13, 12, 11% by weight of the fiber material. So the preferred range contains 20, 21, 22, 23, 24, 25, 26, 27, 28, 29 to 100% by weight of the hydrogel-forming polymer according to the invention, the more preferred range 30, 31, 32, 33, 34, 35, 36, 37, 38, 39 to 100% by weight of the hydrogel-forming polymer according to the invention, the even more preferred range 40, 41, 42, 43, 44, 45, 46, 47, 48, 49 to 100% by weight of hydrogel-forming polymer according to the invention, the much more preferred range 50, 51, 52, 53, 54, 55, 56, 57, 58, 59 to 100% by weight of hydrogel-forming polymer according to the invention, the particularly preferred range 60, 61, 62, 63, 64, 65, 66, 67, 68, 69 to 100% by weight of hydrogel-forming polymer according to the invention, the especially preferred range 70, 71, 71, 72, 73, 74, 75, 76, 77, 78, 79 to 100% by weight of hydrogel-forming polymer according to the invention and the most preferred range 90, 91, 92, 93, 94, 95, 96, 97, 98, 99 or 100% by weight of hydrogel-forming polymer according to the invention.

Hygiene articles for the purposes of the present invention include not only incontinence pads and incontinence briefs for adults but also diapers for infants.

The liquid pervious topsheet (A) is the layer which is in direct contact with the skin of the wearer. Its material comprises customary synthetic or manufactured fibers or films of polyesters, polyolefins, rayon or natural fibers such as cotton. In the case of non-woven materials the fibers are generally joined together by binders such as polyacrylates. Preferred materials are polyesters, rayon or blends thereof, polyethylene and polypropylene. Examples of liquid pervious layers are described in WO 99/57355 A1, EP 102 388 3 A2.

The liquid impervious layer (B) is generally a sheet of polyethylene or polypropylene.

The core (C) includes not only the hydrogel-forming polymer of the invention but also hydrophilic fiber material. By hydrophilic is meant that aqueous fluids spread quickly over the fiber. The fiber material is usually a cellulose, modified cellulose, rayon, polyester such as polyethylene terephthalate. Particular preference is given to cellulose fibers such as pulp. The fibers generally have a diameter of 1–200 µm, and preferably 10–100 µm, and also have a minimum length of 1 mm.

Diaper construction and shape is common knowledge and described for example in WO 95/26209 page 66 line 34 to page 69 line 11, DE 196 04 601 A1, EP-A-0 316 518 and EP-A-0 202 127. Diapers and other hygiene articles are generally also described in WO 00/65084, especially at pages 6–15, WO 00/65348, especially at pages 4–17, WO 00/35502, especially pages 3–9, DE 19737434, WO 98/8439. Hygiene articles for feminine hygiene are described in the following references. The inventive hydrogel-forming polymers capable of absorbing aqueous fluids can be used there. Femcare references: WO 95/24173: Absorption Article for Controlling Odour, WO 91/11977: Body Fluid Odour Control, EP 389023: Absorbent Sanitary Articles, WO 94/25077: Odour Control Material, WO 97/01317: Absorbent Hygienic Article, WO 99/18905, EP 834297, U.S. Pat. No. 5,762,644, U.S. Pat. No. 5,895,381, WO 98/57609, WO 2000/065083, WO 2000/069485, WO 2000/069484, WO 2000/069481, U.S. Pat. No. 6,123,693, EP 1104666, WO 2001/024755, WO 2001/000115, EP 105373, WO 2001/041692, EP 1074233. Tampons are described in the following references: WO 98/48753, WO 98/41179, WO 97/09022, WO 98/46182, WO 98/46181, WO 2001/043679, WO 2001/043680, WO 2000/061052, EP 1108408, WO 2001/033962, DE 200020662, WO 2001/001910, WO 2001/001908, WO 2001/001909, WO 2001/001906, WO 2001/001905, WO 2001/24729. Incontinence articles are described in the following references: Disposable Absorbent Article for Incontinent Individuals: EP 311344 description pages 3–9; Disposable Absorbent Article: EP 850623; Absorbent Article: WO 95/26207; Absorbent Article: EP 894502; Dry Laid Fibrous Structure: EP 850 616; WO 98/22063; WO 97/49365; EP 903134; EP 887060; EP 887059; EP 887058; EP 887057; EP 887056; EP 931530; WO 99/25284; WO 98/48753. Femcare and incontinence articles are described in the following references: Catamenial Device: WO 93/22998 description pages 26–33; Absorbent Members for Body Fluids: WO 95/26209 description pages 36–69; Disposable Absorbent Article: WO 98/20916 description pages 13–24; Improved Composite Absorbent Structures: EP 306262 description pages 3–14; Body Waste Absorbent Article: WO 99/45973. These references and the references therein are hereby expressly incorporated in the disclosure of the present invention.

The hydrogel-forming polymers according to the invention are very useful as absorbents for water and aqueous fluids, so that they may be used with advantage as a water retainer in market gardening, as a filter aid and particularly as an absorbent component in hygiene articles such as diapers, tampons or sanitary napkins.

Incorporation and fixation of the highly swellable hydrogels according to the invention In addition to the above-described highly swellable hydrogels, the absorbent composition of the present invention includes constructions which include highly swellable hydrogels or to which they are fixed. Any construction is suitable that is capable of accommodating highly swellable hydrogels and of being integrated into the absorption layer. A multiplicity of such compositions is already known and described in detail in the literature. A construction for installing the highly swellable hydrogels can be for example a fiber matrix consisting of a cellulose fiber mixture (air-laid web, wet laid web) or of synthetic polymer fibers (meltblown web, spunbonded web) or else of a fiber blend of cellulose fibers and synthetic fibers. Possible fiber materials are detailed in the chapter which follows. The air-laid web process is described for example in WO 98/28 478. Furthermore, open-celled foams or the like may be used to install highly swellable hydrogels.

Alternatively, such a construction can be the result of fusing two individual layers to form one or better a multiplicity of chambers which contain the highly swellable hydrogels. Such a chamber system is described in detail in EP 0 615 736 A1 page 7 lines 26 et seq.

In this case, at least one of the two layers should be water pervious. The second layer may either be water pervious or water impervious. The layer material used may be tissues or other fabric, closed or open-celled foams, perforated films, elastomers or fabrics composed of fiber material. When the absorbent composition consists of a construction of layers, the layer material should have a pore structure whose pore dimensions are small enough to retain the highly swellable hydrogel particles. The above examples of the construction of the absorbent composition also include laminates composed of at least two layers between which the highly swellable hydrogels are installed and fixed.

Generally it is possible to fix hydrogel particles within the absorbent core to improve dry and wet integrity. Dry and wet integrity describes the ability to install highly swellable hydrogels into the absorbent composition in such a way that they withstand external forces not only in the wet but also in the dry state and highly swellable polymer does not dislocate or spill out. The forces referred to are especially mechanical stresses as occur in the course of moving about while wearing the hygiene article or else the weight pressure on the hygiene article in the case of incontinence especially. As to fixation, one skilled in the art knows a multiplicity of possibilities. Examples such as fixation by heat treatment, addition of adhesives, thermoplastics, binder materials are noted in WO 95/26 209 page 37 line 36 to page 41 line 14. The cited passage is thus part of this invention. Methods for enhancing wet strength are also to be found in WO 2000/36216 A1.

Furthermore, the absorbent composition may comprise a base material, for example a polymer film on which the highly swellable hydrogel particles are fixed. The fixing may be effected not only on one side but also on both sides. The base material can be water pervious or water impervious.

The above constructions of the absorbent composition incorporate the highly swellable hydrogels at a weight fraction of from 10–100% by weight, preferably 20–100% by weight, more preferably 30–100% by weight, even more preferably 40–100% by weight, much more preferably 50–100% by weight, particularly preferably 60–100% by weight, especially preferably 70–100% by weight, extremely preferably 80–100% by weight and most preferably 90–100% by weight, based on the total weight of the construction and of the highly swellable hydrogels.

Fiber Materials of the Absorbent Composition

The structure of the present absorbent composition according to the invention may be based on various fiber materials, which are used as a fiber network or matrices. The present invention includes not only fibers of natural origin (modified or unmodified) but also synthetic fibers.

A detailed overview of examples of fibers which can be used in the present invention is given in WO 95/26 209 page 28 line 9 to page 36 line 8. The cited passage is thus part of this invention.

Examples of cellulose fibers include cellulose fibers which are customarily used in absorption products, such as fluff pulp and cellulose of the cotton type. The materials (soft- or hardwoods), production processes such as chemical pulp, semichemical pulp, chemothermo-mechanical pulp (CTMP) and bleaching processes are not particularly restricted. For instance, natural cellulose fibers such as cotton, flax, silk, wool, jute, ethylcellulose and cellulose acetate are used.

Suitable synthetic fibers are produced from polyvinyl chloride, polyvinyl fluoride, polytetrafluoroethylene, polyvinylidene chloride, polyacrylic compounds such as ORLON®, polyvinyl acetate, polyethyl vinyl acetate, soluble or insoluble polyvinyl alcohol. Examples of synthetic fibers include thermoplastic polyolefin fibers, such as polyethylene fibers (PULPEX®), polypropylene fibers and polyethylene-polypropylene bicomponent fibers, polyester fibers, such as polyethylene terephthalate fibers (DACRON® or KODEL®), copolyesters, polyvinyl acetate, polyethyl vinyl acetate, polyvinyl chloride, polyvinylidene chloride, polyacrylics, polyamides, copolyamides, polystyrene and copolymers of the aforementioned polymers and also bicomponent fibers composed of polyethylene terephthalate-polyethylene-isophthalate copolymer, polyethyl vinyl acetate/polypropylene, polyethylene/polyester, polypropylene/polyester, copolyester/polyester, polyamide fibers (nylon), polyurethane fibers, polystyrene fibers and polyacrylonitrile fibers. Preference is given to polyolefin fibers, polyester fibers and their bicomponent fibers. Preference is further given to thermally adhesive bicomponent fibers composed of polyolefin of the core-sheath type and side-by-side type on account of their excellent dimensional stability following fluid absorption.

The synthetic fibers mentioned are preferably used in combination with thermoplastic fibers. In the course of the heat treatment, the latter migrate to some extent into the matrix of the fiber material present and so constitute bond sites and renewed stiffening elements on cooling. Additionally the addition of thermoplastic fibers means that there is an increase in the present pore dimensions after the heat treatment has taken place. This makes it possible, by continuous addition of thermoplastic fibers during the formation of the absorbent core, to continuously increase the fraction of thermoplastic fibers in the direction of the topsheet, which results in a similarly continuous increase in the pore sizes. Thermoplastic fibers can be formed from a multiplicity of thermoplastic polymers which have a melting point of less than 190° C., preferably in the range from 75° C. to 175° C. These temperatures are too low for damage to the cellulose fibers to be likely.

Lengths and diameters of the above-described synthetic fibers are not particularly restricted, and generally any fiber from 1 to 200 mm in length and from 0.1 to 100 denier (gram per 9 000 meters) in diameter may preferably be used. Preferred thermoplastic fibers are from 3 to 50 mm in length, particularly preferred thermoplastic fibers are from 6 to 12 mm in length. The preferred diameter for the thermoplastic fiber is in the range from 1.4 to 10 decitex, and the range from 1.7 to 3.3 decitex (gram per 10 000 meters) is particularly preferred. The form of the fiber may vary; examples include woven types, narrow cylindrical types, cut/chopped yarn types, staple fiber types and continuous filament fiber types.

The fibers in the absorbent composition of the invention can be hydrophilic, hydrophobic or a combination thereof. According to the definition of Robert F. Gould in the 1964 American Chemical Society publication "Contact angle, wettability and adhesion", a fiber is referred to as hydrophilic when the contact angle between the liquid and the fiber (or the fiber surface) is less than 90° or when the liquid tends to spread spontaneously on the same surface. The two processes are generally coexistent. Conversely, a fiber is termed hydrophobic when a contact angle of greater than 90° is formed and no spreading is observed.

Preference is given to using hydrophilic fiber material. Particular preference is given to using fiber material which is weakly hydrophilic on the body side and most hydrophilic in the region surrounding the highly swellable hydrogels. In the manufacturing process, layers having different hydrophilicities are used to create a gradient which channels impinging fluid to the hydrogel, where it is ultimately absorbed.

Suitable hydrophilic fibers for use in the absorbent composition of the invention include for example cellulose fibers, modified cellulose fibers, rayon, polyester fibers, for example polyethylene terephthalate (DACRON®), and hydrophilic nylon (HYDROFIL®). Suitable hydrophilic fibers may also be obtained by hydrophilicizing hydrophobic fibers, for example the treatment of thermoplastic fibers obtained from polyolefins (e.g. polyethylene or polypropylene, polyamides, polystyrenes, polyurethanes, etc.) with surfactants or silica. However, for cost reasons and ease of availability, cellulosic fibers are preferred.

The highly swellable hydrogel particles are embedded into the fiber material described. This can be done in various ways, for example by using the hydrogel material and the fibers together to create an absorbent layer in the form of a matrix, or by incorporating highly swellable hydrogels into fiber mixture layers, where they are ultimately fixed, whether by means of adhesive or lamination of the layers.

The fluid-acquiring and -distributing fiber matrix may comprise synthetic fiber or cellulosic fiber or a mixture of synthetic fiber and cellulosic fiber, in which case the mixing ratio may vary from (100 to 0) synthetic fiber: (0 to 100) cellulosic fiber. The cellulosic fibers used may additionally have been chemically stiffened to increase the dimensional stability of the hygiene article.

The chemical stiffening of cellulosic fibers may be provided in different ways. A first way of providing fiber stiffening is by adding suitable coatings to the fiber material. Such additives include for example polyamide-epichlorohydrin coatings (Kymene® 557 H, Hercoles, Inc. Wilmington, Del.), polyacrylamide coatings (described in U.S. Pat. No. 3,556,932 or as the Parez® 631 NC commercial product from American Cyanamid Co., Stamford, Conn.), melamine-formaldehyde coatings and polyethyleneimine coatings.

Cellulosic fibers may also be chemically stiffened by chemical reaction. For instance, suitable crosslinker substances may be added to effect crosslinking taking place within the fiber. Suitable crosslinker substances are typical substances used for crosslinking monomers including but not limited to $C_2$–$C_8$-dialdehydes, $C_2$–$C_8$-monoaldehydes having acid functionality and in particular $C_2$–$C_9$-polycarboxylic acids. Specific substances from this series are for example glutaraldehyde, glyoxal, glyoxylic acid, formaldehyde and citric acid. These substances react with at least 2 hydroxyl groups within any one cellulose chain or between two adjacent cellulose chains within any one cellulose fiber. The crosslinking causes a stiffening of the fibers, to which greater dimensional stability is imparted as a result of this treatment. In addition to their hydrophilic character, these fibers exhibit uniform combinations of stiffening and elasticity. This physical property makes it possible to retain the capillary structure even under simultaneous contact with fluid and compressive forces and to prevent premature collapse.

Chemically crosslinked cellulose fibers are known and described in WO 91/11162, U.S. Pat. No. 3,224,926, U.S. Pat. No. 3,440,135, U.S. Pat. No. 3,932,209, U.S. Pat. No. 4,035,147, U.S. Pat. No. 4,822,453, U.S. Pat. No. 4,888,093, U.S. Pat. No. 4,898,642 and U.S. Pat. 5,137,537. The chemical crosslinking imparts stiffening to the fiber material, which is ultimately reflected in improved dimensional stability for the hygiene article as a whole. The individual layers are joined together by methods known to one skilled in the art, for example intermelting by heat treatment, addition of hot-melt adhesives, latex binders, etc.

Methods of Making the Absorbent Composition

The absorbent composition is composed of constructions which contain highly swellable hydrogels and the highly swellable hydrogels which are present in said constructions or fixed thereto.

Examples of processes to obtain an absorbent composition comprising for example a base material to which highly swellable hydrogels are fixed on one or both sides are known and included by the invention but not limited thereto.

Examples of processes to obtain an absorbent composition comprising for example a fiber material blend of synthetic fibers (a) and cellulose fibers (b) embedded in highly swellable hydrogels (c), the blend ratio varying from (100 to 0) synthetic fiber: (0 to 100) cellulose fiber, include (1) a process where (a), (b) and (c) are mixed together at one and the same time, (2) a process where a mixture of (a) and (b) is mixed into (c), (3) a process where a mixture of (b) and (c) is mixed with (a), (4) a process where a mixture of (a) and (c) is mixed into (b), (5) a process where (b) and (c) are mixed and (a) is continuously metered in, (6) a process where (a) and (c) are mixed and (b) is continuously metered in, and (7) a process where (b) and (c) are mixed separately into (a). Of these examples, processes (1) and (5) are preferred. The apparatus used in this process is not particularly restricted and any customary apparatus known to one skilled in the art can be used.

The absorbent composition obtained in this way can optionally be subjected to a heat treatment, so that an absorption layer having excellent dimensional stability in the moist state is obtained. The heat treatment process is not particularly restricted. Examples include heat treatment by feeding hot air or infrared irradiation. The temperature of the heat treatment is in the range from 60° C. to 230° C., preferably from 100° C. to 200° C., particularly preferably from 100° C. to 180° C.

The duration of the heat treatment depends on the type of synthetic fiber, its amount and the hygiene article production rate. Generally the duration of the heat treatment is in the range from 0.5 second to 3 minutes, preferably from 1 second to 1 minute.

The absorbent composition is generally provided for example with a liquid-pervious topsheet and a liquid-impervious backsheet. Furthermore, leg cuffs and adhesive tabs are attached to finalize the hygiene article. The materials and types of pervious topsheet and impervious backsheet and of the leg cuffs and adhesive tabs are known to one skilled in the art and are not particularly restricted. Examples thereof may be found in WO 95/26 209.

Experimental Part

The quality of the surface crosslinking can be determined by subjecting the dried hydrogel to the following test methods:

Test Methods a) Centrifuge Retention Capacity (CRC)

This method measures the free swellability of the hydrogel in a teabag. 0.2000±0.0050 g of dried hydrogel (particle size fraction 106–850 μm) are weighed into a teabag 60×85 mm in size which is subsequently sealed. The teabag is placed for 30 minutes in an excess of 0.9% by weight sodium chloride solution (at least 0.83 l of sodium chloride solution/1 g of polymer powder). The teabag is then centrifuged for 3 minutes at 250 g. The amount of liquid is determined by weighing back the centrifuged teabag.

b) Absorbency Under Load (AUL) (0.7 psi)

The measuring cell for determining AUL 0.7 psi is a Plexiglass cylinder 60 mm in internal diameter and 50 mm in height. Adhesively attached to its underside is a stainless steel sieve bottom having a mesh size of 36 μm. The measuring cell further includes a plastic plate having a diameter of 59 mm and a weight which can be placed in the measuring cell together with the plastic plate. The plastic plate and the weight together weigh 1 345 g. AUL 0.7 psi is determined by determining the weight of the empty Plexiglass cylinder and of the plastic plate and recording it as $W_0$. 0.900±0.005 g of hydrogel-forming polymer (particle size distribution 150–800 μm) is then weighed into the Plexiglass cylinder and distributed very uniformly over the stainless steel sieve bottom. The plastic plate is then carefully placed in the Plexiglass cylinder, the entire unit is weighed and the weight is recorded as $W_a$. The weight is then placed on the plastic plate in the Plexiglass cylinder. A ceramic filter plate 120 mm in diameter and 0 in porosity is then placed in the middle of a Petri dish 200 mm in diameter and 30 mm in height and sufficient 0.9% by weight sodium chloride solution is introduced for the surface of the liquid to be level with the filter plate surface without the surface of the filter plate being wetted. A round filter paper 90 mm in diameter and <20 μm in pore size (S&S 589 Schwarzband from Schleicher & Schüll) is subsequently placed on the ceramic plate. The Plexiglass cylinder containing hydrogel-forming polymer is then placed with plastic plate and weight on top of the filter paper and left there for 60 minutes. At the end of this period, the complete unit is removed from the filter paper and the Petri dish and subsequently the weight is removed from the Plexiglass cylinder. The Plexiglass cylinder containing swollen hydrogel is weighed together with the plastic plate and the weight recorded as $W_b$.

AUL was calculated by the following equation:

$$AUL\ 0.7\ psi\ [g/g]=[W_b-W_a]/[W_a-W_0]$$

AUL-0.5 psi is measured using a correspondingly lower pressure.

c) Saline Flow Conductivity (SFC)

The test method for determining SFC is described in U.S. Pat. No. 5,599,335.

EXAMPLES

Preparation Example for N-2-hydroxyethylmorpholine-2,3-dione:

657.6 g (4.5 mol) of diethyl oxalate are initially charged to a 2 l four-neck flask equipped with reflux condenser, thermometer, KPG stirrer and dropping funnel and are heated to 80° C.

473.1 g (4.5 mol) of diethanolamine are added dropwise in the course of 2 h. After supplementary stirring at 80° C. for 2 h, the released ethanol is removed under reduced pressure to obtain about 749.4 g of almost colorless residue which still contains traces of ethanol.

For further purification, 717.4 g of the crude product are dissolved in 1.8 l of ethanol at the heat of boiling. After cooling to room temperature, the crystals are filtered off with suction on a Büchner funnel and washed twice with 200 ml of ice-cold ethanol each time. Drying under reduced pressure leaves 502.4 g (3.15 mol) of colorless, analytically pure material.

Melting point: 86.5° C. (EtOH).

IR: 3400, 1757, 1682, 1148, 1055 cm−1

Elemental analysis: theory: C, 45.31: H, 5.7: N, 8.8: O, 40.2: found: C, 45.1: H, 5.7: N, 8.8: O, 40.0.

The identity is confirmed by $^1$H and $^{13}$C NMR and also mass spectrometry.

The other morpholine-2,3-dione derivatives can be prepared in similar fashion or by means of literature-known methods.

Hydrogel Making Example 1

In a 40 l plastic bucket, 6.9 kg of glacial acrylic acid are diluted with 23 kg of water in which 213 g of starch have been dissolved (Paselli SA 2 from AVEBE-Netherlands). 45 g of pentaerythritol triallyl ether are added to this solution with stirring, and the sealed bucket is inertized by passing nitrogen through it. The polymerization is then initiated by adding about 400 mg of hydrogen peroxide and 200 mg of ascorbic acid. After the reaction has ended, the gel is mechanically comminuted and mixed with sufficient aqueous sodium hydroxide solution to obtain a degree of neutralization of 75 mol %, based on acrylic acid used (192 g of NaOH 50% per kg of gel). The neutralized gel is then dried on a can dryer, ground with a pin mill and finally screened off at 300–800 micrometers.

Hydrogel Making Example 2

A rectangular plastic dish having a base area of about 30×40 cm and inertized by being bound into a PE bag receives an already nitrogen-inertized solution prepared in a separate vessel, via a tube system. The solution is made up of the following components: 1466 g of water, 305 g of acrylic acid, 3204 g of sodium acrylate 37% aqueous, 11 g of SARTOMER SR 9035 (ethoxylated trimethylolpropane triacrylate from SARTOMER—USA), 0.61 g of 2,2-azo-bisamidinopropane dihydrochloride and 3.1 g of sodium persulfate. At the same time as the monomer solution is introduced, 2 further initiator solutions are added via 2 separate tube systems in such a way that homogeneous mixing with the monomer solution takes place. These two further initiator solutions are on the one hand a solution of 0.25 g of hydrogen peroxide in 5 g of water and on the other a solution of 0.25 g of ascorbic acid in 5 g of water. The polymerization reaction gives an approximately 4 cm thick gel block which is mechanically comminuted by means of a meat grinder, dried at 160° C. in a circulating air drying cabinet, ground with an ultracentrifugal mill and subsequently screened off at 300–850 μm.

Hydrogel Making Example 3

Hydrogel making example 2 is repeated except that the monomer solution additionally contains 0.5 g of N-2-hydroxyethyl-morpholine-2,3-dione.

Inventive Example 1

20 g of the base polymer of hydrogel making example 1 are sprayed in a Waring laboratory mixer with a crosslinker solution of the following composition: 1.5% by weight of isopropanol, 3.5% by weight of water, 0.08% by weight of N-2-hydroxyethyl-morpholine-2,3-dione, each based on polymer used. The moist product is subsequently annealed in a circulating air drying cabinet at 175° C. for 60 minutes. The dried product is subsequently screened off at 850 μm to remove clumps.

Comparative Example 1

20 g of the base polymer of hydrogel making example 1 are sprayed in a Waring laboratory mixer with a crosslinker solution of the following composition: 1.5% by weight of isopropanol, 3.5% by weight of water, but without any addition of N-2-hydroxyethyl-morpholine-2,3-dione, each based on polymer used. The moist product is subsequently annealed in a circulating air drying cabinet at 175° C. for 60 minutes. The dried product is subsequently screened off at 850 μm to remove clumps.

Inventive Example 2

20 g of the base polymer of hydrogel making example 2 are sprayed in a Waring laboratory mixer with a crosslinker solution of the following composition: 1.5% by weight of isopropanol, 3.5% by weight of water, 0.08% by weight of N-2-hydroxyethyl-morpholine-2,3-dione, each based on polymer used. The moist product is subsequently annealed in a circulating air drying cabinet at 175° C. for 60 minutes. The dried product is subsequently screened off at 850 μm to remove clumps.

Inventive Example 3

20 g of the base polymer of hydrogel making example 2 are sprayed in a Waring laboratory mixer with a crosslinker solution of the following composition: 1.5% by weight of isopropanol, 3.5% by weight of water, 0.08% by weight of N-methylmorpholine-2,3-dione, each based on polymer used. The moist product is subsequently annealed in a circulating air drying cabinet at 175° C. for 60 minutes. The dried product is subsequently screened off at 850 μm to remove clumps.

Inventive Example 4

20 g of the base polymer of hydrogel making example 2 are sprayed in a Waring laboratory mixer with a crosslinker solution of the following composition: 1.5% by weight of isopropanol, 3.5% by weight of water, 0.08% by weight of N-tert-butyl-morpholine-2,3-dione, each based on polymer used. The moist product is subsequently annealed in a circulating air drying cabinet at 175° C. for 60 minutes. The dried product is subsequently screened off at 850 μm to remove clumps.

Inventive Example 5

20 g of the base polymer of hydrogel making example 2 are sprayed in a Waring laboratory mixer with a crosslinker solution of the following composition: 1.5% by weight of isopropanol, 3.5% by weight of water, 0.08% by weight of N-ethylmorpholine-2,3-dione, each based on polymer used. The moist product is subsequently annealed in a circulating air drying cabinet at 175° C. for 60 minutes. The dried product is subsequently screened off at 850 μm to remove clumps.

Comparative Example 2

20 g of the base polymer of hydrogel making example 2 are sprayed in a Waring laboratory mixer with a crosslinker solution of the following composition: 1.5% by weight of isopropanol, 3.5% by weight of water, but without any addition of morpholine-2,3-dione derivatives as used in inventive examples 2 to 5, each based on polymer used. The moist product is subsequently annealed in a circulating air drying cabinet at 175° C. for 60 minutes. The dried product is subsequently screened off at 850 µm to remove clumps.

Inventive Example 6

20 g of the base polymer of hydrogel making example 3 are sprayed in a Waring laboratory mixer with a crosslinker solution of the following composition: 1.5% by weight of isopropanol, 3.5% by weight of water, 0.08% by weight of N-2-hydroxyethyl-morpholine-2,3-dione, each based on polymer used. The moist product is subsequently annealed in a circulating air drying cabinet at 175° C. for 60 minutes. The dried product is subsequently screened off at 850 µm to remove clumps.

Comparative Example 3

20 g of the base polymer of hydrogel making example 3 are sprayed in a Waring laboratory mixer with a crosslinker solution of the following composition: 1.5% by weight of isopropanol, 3.5% by weight of water, but without any addition of morpholine-2,3-dione derivatives as used in inventive example 6, each based on polymer used. The moist product is subsequently annealed in a circulating air drying cabinet at 175° C. for 60 minutes. The dried product is subsequently screened off at 850 µm to remove clumps.

We claim:

1. A process for crosslinking starting polymers for preparing hydrogel-forming polymers capable of absorbing aqueous fluids, which comprises using a crosslinker of a general formula 1:

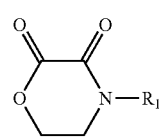

(Formula 1)

where $R_1$ is hydrogen, $C_1$–$C_4$-alkyl, $C_1$–$C_4$-hydroxyalkyl or a group of the formula 2:

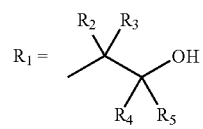

(Formula 2)

where $R_2$, $R_3$, $R_4$, and $R_5$ are each independently $C_1$–$C_4$-alkyl, $C_1$–$C_4$-hydroxyalkyl or hydrogen.

2. The process of claim 1 for surface postcrosslinking of starting polymers containing carboxyl groups, which comprises using a crosslinker of the general formula 1.

3. The process of claim 1 wherein the starting polymer is treated with the crosslinker and postcrosslinked and dried by raising the temperature during or after the treatment, the crosslinker being present in an inert solvent.

TABLE

| Example | Base polymer as per hydrogel preparation example | Crosslinker | CRC (g/g) | AUL 0.5 psi (g/g) | AUL 0.7 psi (g/g) |
|---|---|---|---|---|---|
| Inventive 1 | 1 | 0.08% of N-2-hydroxyethyl-morpholine-2,3-dione | 34.2 | 26.8 | 23.9 |
| Comparative 1 | 1 | — | 38.3 | 9.4 | 8.4 |
| Inventive 2 | 2 | 0.08% of N-2-hydroxyethyl-morpholine-2,3-dione | 35.6 | 25.2 | 19.5 |
| Inventive 3 | 2 | 0.08% of N-methyl-morpholine-2,3-dione | 37.4 | 13.7 | 9.7 |
| Inventive 4 | 2 | 0.08% of N-tert-butyl-morpholine-2,3-dione | 37.2 | 13.2 | 8.9 |
| Inventive 5 | 2 | 0.08% of N-ethyl-morpholine-2,3-dione | 37.4 | 13.2 | 12.9 |
| Comparative 2 | 2 | — | 39.7 | 7.9 | 6.5 |
| Inventive 6 | 3 | 0.08% of N-2-hydroxyethyl-morpholine-2,3-dione | 34.0 | 27.6 | 24.2 |
| Comparative 3 | 3 | — | 36.5 | 12.1 | 8.5 |

4. The process of claim 1 wherein the crosslinker is N-hydroxyethyl-2,3-morpholinedione.

5. The process of claim 1 wherein the starting polymer is a polymeric acrylic acid or a polyacrylate.

6. The process of claim 1 wherein a composition comprising the crosslinker and a solvent is used in a ratio of 0.1–20% by weight based on the mass of the starting polymer.

7. The process of claim 1 wherein the crosslinker is used in a dose of 0.01–5.0% by weight, based on the starting polymer.

8. The process of claim 5 wherein the polymeric acrylic acid or the polyacrylate is crosslinked in a free radical polymerization using a polyfunctional ethylenically unsaturated crosslinker.

9. The process of claim 1 wherein the crosslinker of the general formula 1 is admixed with a solvent selected from the group consisting of water, a mixture of water with one or more organic solvents having unlimited solubility in water, and a mixture of water with one or more monohydric or polyhydric alcohols.

10. The process of claim 6 wherein the composition is used in a ratio of 0.5–10% by weight based on the mass of the starting polymer.

11. The process of claim 1 wherein the crosslinker is used in a dose of 0.02–3.0% by weight, based on the starting polymer.

12. The process of claim 1 wherein the crosslinker is used in a dose of 0.03–1.0% by weight, based on the starting polymer.

13. The process of claim 1 wherein the crosslinker is used in a dose of 0.05–0.1% by weight, based on the starting polymer.

* * * * *

UNITED STATES PATENT AND TRADEMARK OFFICE
CERTIFICATE OF CORRECTION

PATENT NO. : 7,183,360 B2  Page 1 of 1
APPLICATION NO. : 10/491204
DATED : February 27, 2007
INVENTOR(S) : Thomas Daniel et al.

It is certified that error appears in the above-identified patent and that said Letters Patent is hereby corrected as shown below:

On the Title Page:

Item (30), "101 49 267" should be -- 101 49 267.7 --.

Signed and Sealed this

Second Day of October, 2007

JON W. DUDAS
*Director of the United States Patent and Trademark Office*